United States Patent
Tu et al.

(10) Patent No.: US 9,986,938 B2
(45) Date of Patent: Jun. 5, 2018

(54) METHOD AND DEVICE FOR DETERMINING A GEOMETRICAL PARAMETER OF A BLOOD VESSEL

(71) Applicant: MEDIS ASSOCIATED B.V., Leiden (NL)

(72) Inventors: Shengxian Tu, Leiden (NL); Johan Hendrikus Christiaan Reiber, Leiden (NL)

(73) Assignee: MEDIS ASSOCIATED B.V., Leiden (NL)

( * ) Notice: Subject to any disclaimer, the term of this patent is extended or adjusted under 35 U.S.C. 154(b) by 0 days. days.

(21) Appl. No.: 14/189,693

(22) Filed: Feb. 25, 2014

(65) Prior Publication Data

US 2015/0238121 A1    Aug. 27, 2015

(51) Int. Cl.
| | | |
|---|---|---|
| *A61B 8/00* | (2006.01) | |
| *A61B 5/107* | (2006.01) | |
| *A61B 5/00* | (2006.01) | |
| *A61B 5/02* | (2006.01) | |
| *A61B 8/12* | (2006.01) | |
| *A61B 8/08* | (2006.01) | |
| *A61B 8/14* | (2006.01) | |

(52) U.S. Cl.
CPC .......... *A61B 5/1076* (2013.01); *A61B 5/0066* (2013.01); *A61B 5/0084* (2013.01); *A61B 5/02007* (2013.01); *A61B 5/1079* (2013.01); *A61B 8/0891* (2013.01); *A61B 8/12* (2013.01); *A61B 8/14* (2013.01); *A61B 8/523* (2013.01)

(58) Field of Classification Search
CPC . A61B 5/1076; A61B 5/02007; A61B 5/0066; A61B 5/0084; A61B 5/1079; A61B 8/523; A61B 8/14; A61B 8/0891; A61B 8/12

USPC .................................................. 600/407–480
See application file for complete search history.

(56) References Cited

U.S. PATENT DOCUMENTS

| | | | |
|---|---|---|---|
| 2006/0149522 A1 | 7/2006 | Tang | |
| 2010/0185079 A1* | 7/2010 | Huizenga .............. | A61B 5/055 600/410 |

(Continued)

OTHER PUBLICATIONS

EuroIntervention Abstract, "Three-dimensional rendering of OCT pullbacks for assessment of side-branch ostia," *EAPCI* (2013).

(Continued)

*Primary Examiner* — Sanjay Cattungal
(74) *Attorney, Agent, or Firm* — Barnes & Thornburg LLP; Mark J. Nahnsen (57) ABSTRACT

The various aspects relate to a method of determining a geometrical parameter of a side branch of a main branch of a blood vessel, comprising receiving a multitude of cross section data sets, the data sets representing geometries of cross sections of the main branch over a length of the main branch and receiving position data of a cut plane of the main branch, the cut plane intersecting the side branch and the cut plane being defined under an angle with the cross-sections. The method further comprises, based on data in at least a part of the cross section data sets, constructing image data of a constructed cross section of the main branch in the cut plane. The method comprises receiving contour data defining a contour in the constructed cross section, the contour being provided in the side branch and determining the parameter by determining a parameter of the contour.

14 Claims, 5 Drawing Sheets

(56) References Cited

U.S. PATENT DOCUMENTS

| | | | |
|---|---|---|---|
| 2011/0178383 A1 | 7/2011 | Kassab | |
| 2011/0240852 A1* | 10/2011 | Tanner | G01N 1/286 |
| | | | 250/307 |
| 2011/0295579 A1 | 12/2011 | Tang | |
| 2012/0083696 A1 | 4/2012 | Kitamura | |
| 2012/0084064 A1 | 4/2012 | Dzenis | |
| 2012/0130243 A1 | 5/2012 | Balocco et al. | |
| 2012/0296214 A1* | 11/2012 | Urabe | A61B 8/0858 |
| | | | 600/444 |
| 2013/0028494 A1 | 1/2013 | Groth | |
| 2013/0090555 A1 | 4/2013 | Kassab | |
| 2014/0029821 A1* | 1/2014 | Lee | G06T 7/0012 |
| | | | 382/131 |
| 2014/0257087 A1* | 9/2014 | Elbasiony | A61B 5/061 |
| | | | 600/424 |
| 2015/0245776 A1* | 9/2015 | Hirohata | A61B 6/032 |
| | | | 600/504 |
| 2015/0356734 A1* | 12/2015 | Ooga | A61B 6/03 |
| | | | 382/131 |

OTHER PUBLICATIONS

Hahn et al., "Comparison of vessel geometry in bifurcation between normal and diseased segments: Intravascular ultrasound analysis," *Atherosclerosis*, 201: 326-331 (2008).
Medis Specials, "QAnglo® OCT Research Edition v1.0," (2012).
Pyxaras et al., "Optimization of Tryton Dedicated Coronary Bifurcation System with Coregistration of Optical Coherence Tomography and Fractional Flow Reserve," *JACC Cardio. Interventions*, 6(7): e39-40 (2013).
Wang et al., "Computerized Medical Imaging and Graphics," *Elsevier*, 38: 113-122 (2014).

\* cited by examiner

METHOD AND DEVICE FOR DETERMINING A GEOMETRICAL PARAMETER OF A BLOOD VESSEL

TECHNICAL FIELD

The various aspects relate to a method and device for determining at least one geometrical parameter of a side branch of a main branch of a blood vessel.

BACKGROUND

Evaluation of a side branch ostium in coronary bifurcation lesions is challenging in clinical practice and science. Various methods of obtaining data by means of invasive methods are known, like Optical Coherence Tomography—OCT—and Intravascular Ultrasound—IVUS. Such methods require intervention in blood vessels of the human body. Although a skilled cardiologist is able to control such techniques without much risk, there still is a risk connected to such techniques, in particular a risk of damaging walls of blood vessels.

Therefore, the least amount of invasive actions is preferred. This means it is advantageous to be able to obtain data on the ostium—or opening or cross section—of a specific blood vessel by means of data obtained from another blood vessel of which the specific blood vessel is a side branch. In the paper "First Presentation of 3-Dimensional Recontruction and Centerline-Guided Assessment of Coronary Bifurcation by Fusion of X-Ray Angiography and Optical Coherence Tomography" in the JACC Cardiovascular Interventions journal, a method is proposed by fusing data obtained by means of x-ray angiography—XA—and data obtained by means of OCT. With XA data, a centreline of a sidebranch of a coronary vessel is determined. Subsequently, using OCT data obtained in the main branch, the area of the ostium of the side branch is determined in a plane perpendicular to the centreline determined via the XA data.

SUMMARY

It is preferred to determine the ostium of a blood vessel based on data obtained by means of one analysis technique.

A first aspect provides method of determining at least one geometrical parameter of a side branch of a main branch of a blood vessel. The method comprises receiving a multitude of cross section data sets, the data sets representing geometries of cross sections of the main branch over a length of the main branch and receiving position data of a cut plane of the main branch, the cut plane at least partially intersecting the side branch and the cut plane being defined under an angle with the cross-sections. The method further comprises, based on data in at least a part of the multitude of cross section data sets, constructing image data of a constructed cross section of the main branch in the cut plane. The method also comprises receiving contour data defining a contour in the constructed cross section, the contour being provided in the side branch and determining the geometrical parameter by determining a geometrical parameter of the contour.

This method may be carried out using OCT or IVUS data only, thus removing a need for XA data and the fusion procedure. XA data requires injection of a contrast fluid as well as x-ray photography or filming. This means the method as outlined above removes the need of another analysis method for which intervention of the patient is required. Furthermore, as only OCT or IVUS data is used, less processing power is required as no XA data is to be processed.

Furthermore, as the resolution of OCT or IVUS data is higher than of XA data, this method is more accurate.

In an embodiment of the first aspect, receiving the definition of the cut plane comprises: receiving a longitudinal angle of the cut plane, the longitudinal angle being defined between the cut plane and an axis of the main branch; and receiving a transversal angle of the cut plane, the transversal angle being defined between the cut plane and a direction perpendicular to the axis of the main branch.

By using the main branch as a reference for the cut plane, rather than the side branch, using OCT or IVUS data obtained in the main branch suffices and no data on the side branch is required.

Another embodiment of the first aspect comprises based on the multitude of cross section data sets, generating first image data for display of a first two-dimensional view of the main branch in a longitudinal direction. This embodiment further comprises receiving longitudinal location data of the cut plane indicating a location of the cut plane in the first two-dimensional view; based on the multitude of cross section data sets, generating second image data for display of a second two-dimensional view of the main branch in a transversal direction; and receiving transversal location data of the cut plane indicating a location of the cut plane in the second two-dimensional view.

This embodiment allows accurate positioning of the cut plane, based on image data that can be derived from the OCT data without significant processing. For the longitudinal cross section, data from individual tomographic images are merged in one single image. And for the transversal cross section, only one tomographic image is required.

A further embodiment of the first aspect comprises determining a discontinuity in a sequential series of the multitude of cross section data sets and defining the cut plane at the location of the discontinuity as a default location.

A discontinuity in the vessel wall, shown by OCT or IVUS data, may indicate presence of a side branch of the main branch. This information may be used to position the cut plane. The position of the cut plane may be adjusted to obtain more accurate information subsequently.

Yet another embodiment of the first aspect comprises determining increase of a cross section geometry parameter being above a pre-determined threshold; determining a slope of either side of the main branch relative to a centre line of the main branch; determining a first side of the main branch having the largest slope; and defining the cut plane to be positioned perpendicular to the first side.

This embodiment allows for further automation of determining an ostium of the side branch.

A second aspect provides a computer programme product comprising computer executable code that, when loaded in a processing module of a computer, cause the computer to execute the method according to the first aspect.

A third aspect provides a device for determining at least one geometrical parameter of a side branch of a main branch of a blood vessel. The device comprises a data input module arranged to receive a multitude of cross section data sets, the data sets representing geometries of cross sections of the main branch over a length of the main branch. The device further comprises a processing unit arranged to receive position data of a cut plane of the main branch, the cut plane at least partially intersecting the side branch and the cut plane being defined under an angle with the cross-sections; based on data in at least a part of the multitude of cross section data sets, construct image data of a constructed cross section of the main branch in the cut plane; receive contour data defining a contour in the constructed cross section, the contour being provided in the side branch; and determine the geometrical parameter by determining a geometrical parameter of the contour.

BRIEF DESCRIPTION OF THE DRAWINGS

The various aspects and embodiments thereof will now be discussed in conjunction with Figures. In the Figures.

FIG. 7 A: shows cross section of the main branch and the side branch in the cut plane; and FIG. 7 B: shows a detail of the cross section of FIG. 7 A with a contour provided in it.

DETAILED DESCRIPTION

Figure 1:
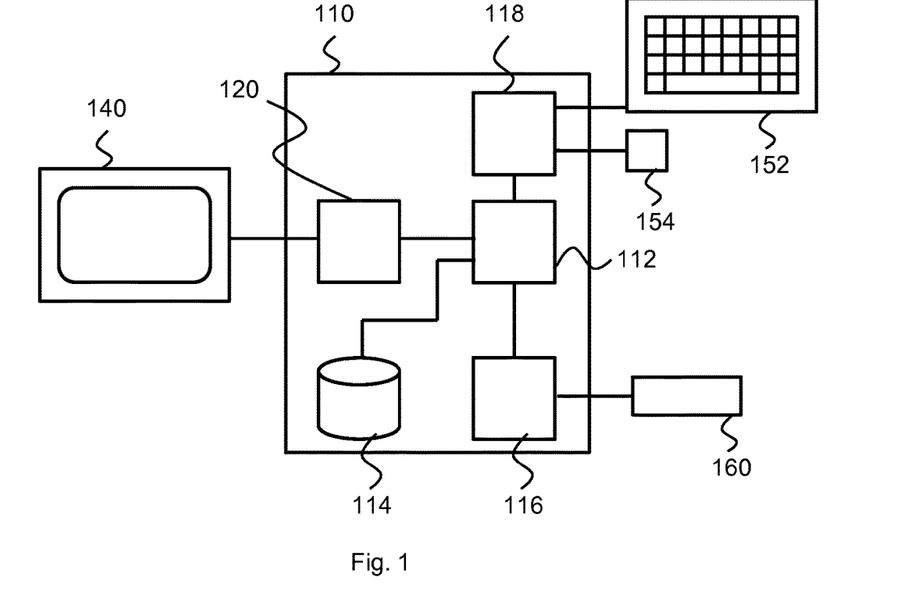
FIG. 1: shows a data analysis device

FIG. 1 shows a data analysis device 110 for processing data obtained by means of Optical Coherence Tomography-OCT. OCT is a method for obtaining image data from within a blood vessel. With OCT, a probe is provided in the vessel and slowly pulled back while collecting data. The data can be obtained from the direct inner surface of the vessel wall, as well as of material deeper in the vessel wall. Output data is obtained in data sets representing 2D images, each image providing a transversal cross section image of the blood vessel. The data analysis device 110 comprises a microprocessor 112 as a processing module, a memory module 114, a measurement processing module 116, a user input module 118 and an image rendering module 120. The microprocessor 112 is arranged for controlling the data analysis device 110 and various components thereof. The memory module is arranged for storing measurement data, processed data and computer executable code enabling the microprocessor 112 to execute methods as discussed below.

The measurement processing module 116 is arranged for receiving raw data from an OCT probe 160 and for providing light—infrared light in particular—to the probe 160 for collecting data. The user input module 118 is arranged for receiving user input data from a keyboard 152 and a mouse 154. The image rendering module 120 is arranged for rendering image data in any format for providing the rendered image in ready to display data to a screen 140. The screen 140 may be provided as a touch screen, enabling a user of the data analysis device 110 to control the data analysis device 110.

Figure 2:
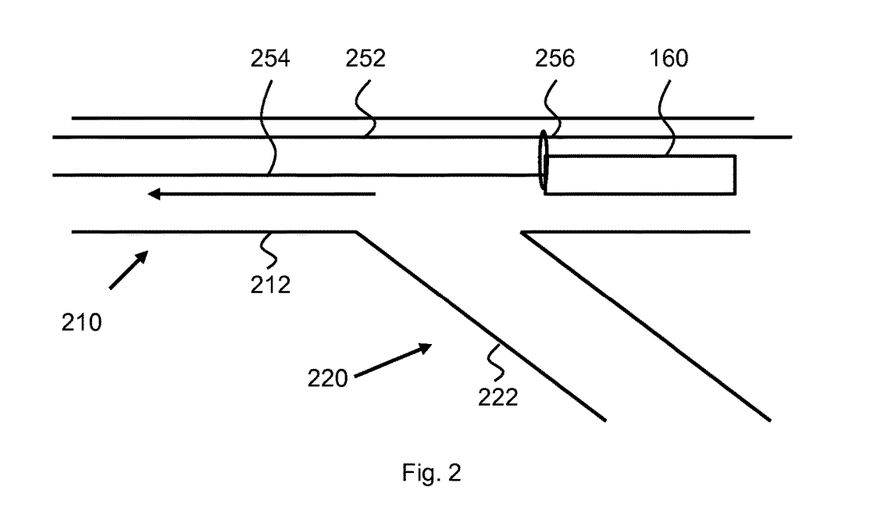
FIG. 2: shows a main branch and a side branch of a coronary artery with an OCT probe.

FIG. 2 shows a first blood vessel 210 as a main branch and a second blood vessel 220 as a side branch. The first blood vessel 210 has a first vessel wall 212 and the second blood vessel 220 has a second vessel wall 222. In the first blood vessel 210, the OCT probe 160 is introduced. To the OCT probe 160, a feed wire 254 is connected for moving the OCT probe 160. The OCT probe 160 is connected to a guide wire 252 for guidance of the probe 160 and for inserting the probe. During acquisition of data, the probe 160 is pulled back through the first blood vessel 210 at a constant velocity. The pulling back is preferably done in a motorised way, using an electromotor controlled by the data analysis device 110.

Using OCT, cross section data of the first blood vessel 210 is obtained. From the cross section data, a cross section dimension of the first blood vessel 210 may be obtained in a relatively accurate way. For accurately determining a cross section dimension of the second blood vessel, ideally the OCT probe 160 is inserted in the second blood vessel 220 as well. A disadvantage of this method, however, is that this may increase a risk of puncture of the first vessel wall 212 of the first blood vessel 210 or the second vessel wall 222 of the second blood vessel 220. Furthermore, this method also increases the workload of a cardiologist.

Figure 3:
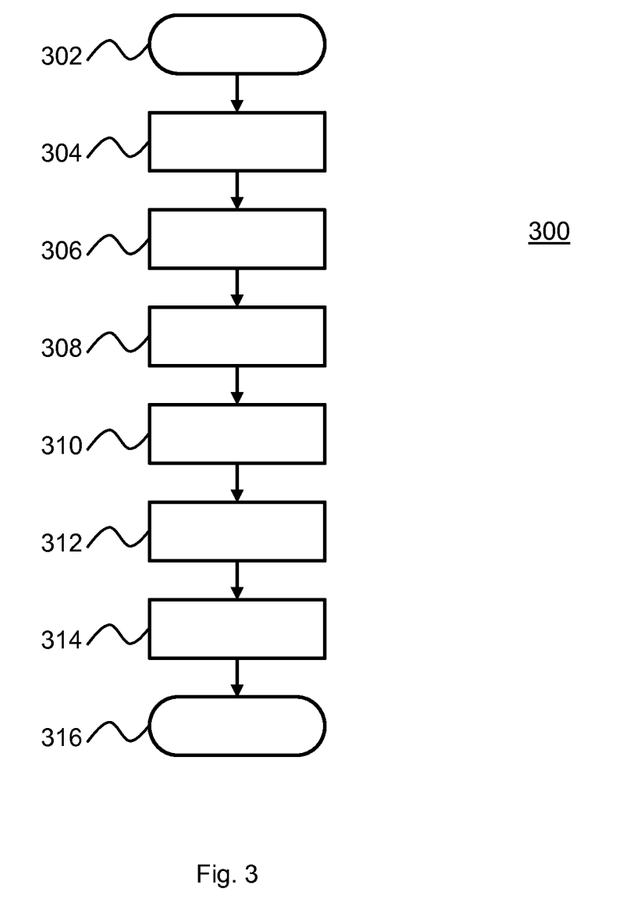
FIG. 3: shows a flowchart depicting a method as embodiment of the first aspect.

FIG. 3 shows a flowchart 300 depicting a method for more accurately determining a cross section geometry of the second blood vessel 220 from OCT measurements of the first blood vessel 210 only.

Figure 4:
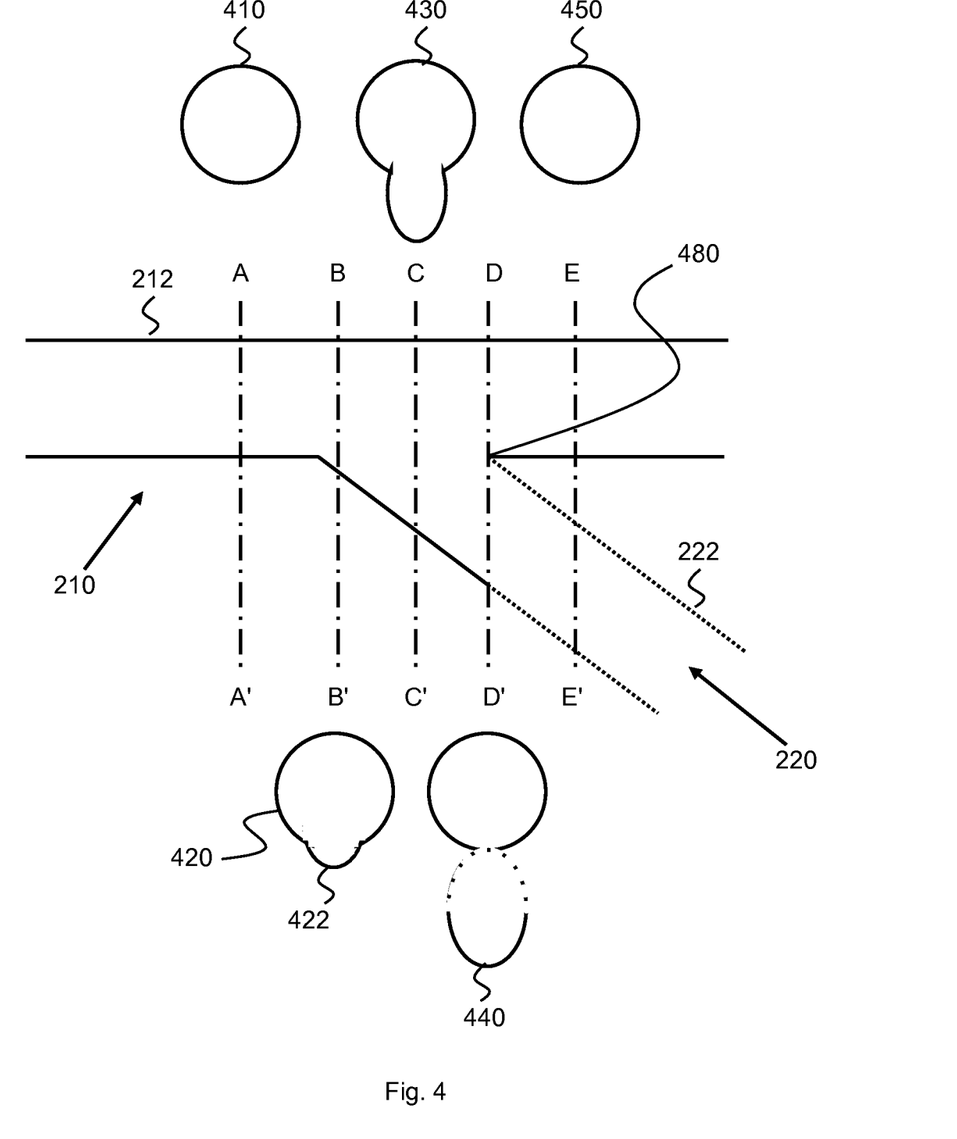
FIG. 4: shows the main branch and the side branch with several transversal cross sections.

The process starts in a terminator 302 and continues to step 304 in which data sets are being received. Data may be buffered by the measurement processing module 116 before storing it in the memory module 114. Alternatively, data received by the measurement processing module 116 is stored directly in the memory module 114. In step 306, a longitudinal cross section image of the main vessel 210 is created. FIG. 4 shows a longitudinal image of the first blood vessel 210 and the second blood vessel.

As data is obtained from a position in the first blood vessel 210, a part of the second vessel wall 222 of the second blood is occluded from the probe 160. This part of the second vessel wall 222 is provided in dotted lines in FIG. 4. The occlusion results in a discontinuity of obtained data at an armpit section 480 between the first blood vessel 210 and the second blood vessel 220. The longitudinal cross section as shown by FIG. 4 is obtained by combining data from multiple sequential transversal cross section data sets in step 306.

The angle under which the longitudinal cross section as shown by FIG. 4 is shown, may be determined by an operator of the data analysis device 110. Alternatively, the angle may be obtained by detecting discontinuities or occlusions in cross section data sets or in the reconstructed 2D image as shown by FIG. 4. Subsequently, the image data is processed such that a discontinuity is shown at the top or bottom of an image. Alternatively, the cut plane 500 may be placed at a random position or a pre-determined default position.

FIG. 4 shows five cross section images of the first blood vessel 210 and the second blood vessel 220. A first cross section image 410 is obtained in a cross section between A and A'. At this location, a substantially circular cross section is found. A second cross section image 420 obtained between B and B' shows a small bulge 422 where the second blood vessel 220 stems from the first blood vessel 210. In a third cross section 420 between C and C', the cross section of the second blood vessel 420 is already larger. A location between D and D' is a last location, from left to right, where data on a part of the second blood vessel 220 may be obtained. Beyond that point, the second blood vessel 220 is occluded by the first vessel wall 212 of the first blood vessel 210.

And already at the armpit section 480, part of the second vessel wall 222 of the second blood vessel 220 is already occluded. This is indicated by a dotted line in the fourth cross section image 440. At the dotted locations, data cannot be obtained by an OCT probe 160 in the first blood vessel 210 as these locations are occluded to the OCT probe 160 by the first vessel wall 212 and the second vessel wall 222. Data of the fifth cross section image 450 obtained between E and E' shows a substantially circular cross section again. Although a cross section of a blood vessel may be approximated by a circle, in practice the cross section will seldom be a perfect circle.

Figure 5:
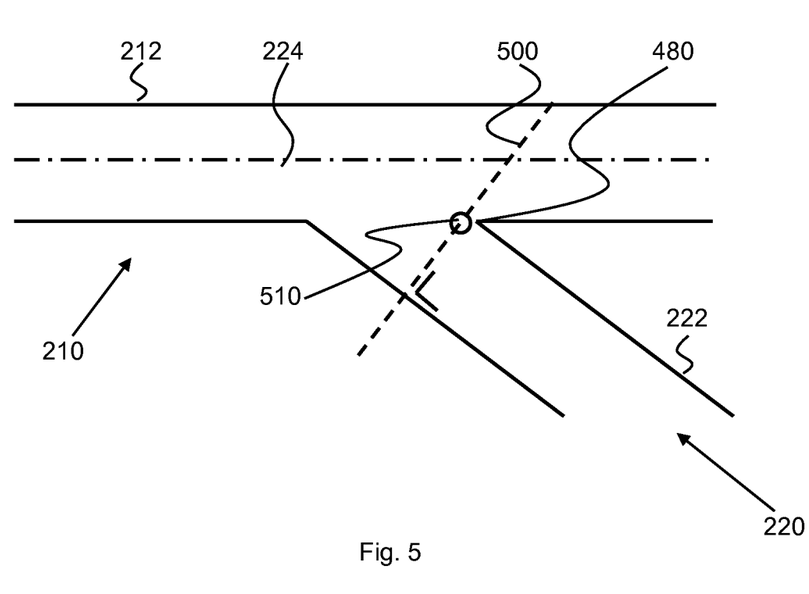
FIG. 5: shows the main branch and the side branch with a cut plane.

After the longitudinal cross section has been obtained, data on a position of a cut plane 500 as shown by FIG. 5 is obtained in step 308. The data may be obtained by means of the keyboard 152, the mouse 154, the touch screen 140, other, or a combination thereof, thus by receiving user input indicating a position of the cut plane 500. Alternatively or additionally, the cut plane provided at a default location in an image. In yet another alternative, the cut plane 500 is provided at or near the armpit section 480. The armpit section 480 may be determined by determining a discontinuity in data obtained on the walls of the vessels on which data is obtained.

Figure 6:
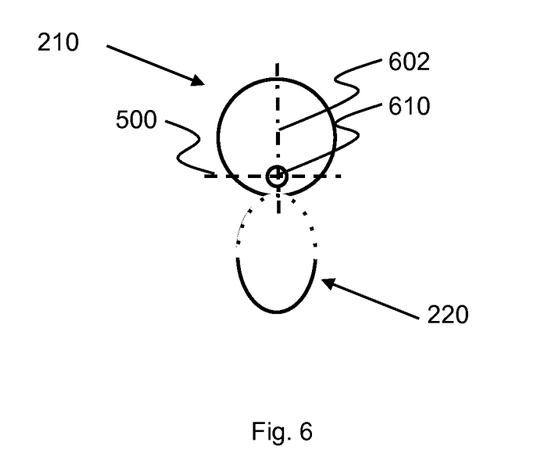
FIG. 6: shows a transversal cross section of the main branch and the side branch.

The cut plane 500 is preferably defined by five parameters: an x-coordinate relative to a reference point in the obtained data, a y-coordinate, a z-coordinate, a first angle of the cut plane relative to a longitudinal axis 224 of the first blood vessel 222 and a second angle of the cut plane 500 relative to a transversal axis 602 shown by FIG. 6. The Cartesian coordinates are preferably coordinates of a hinge point 510 over which the cut plane 500 may be tilted in an image provided by FIG. 5 by means of keyboard 152, the mouse 154, the touch screen 140, other, or a combination thereof.

And the Cartesian coordinates preferably also indicate the hinge point 510 over which the cut plane may be tilted in an image shown by FIG. 6, by means of the keyboard 152, the mouse 154, the touch screen 140, other, or a combination thereof. Also the Cartesian coordinates of the cut plane 500 may be modified using the input means. In this way, an operator of the data analysis device 110 is able to move the cut plane 500 to a location where the operator deems a cross section or other geometry of the second blood vessel 200 may be determined best.

First, a location of the cut plane 500 in the longitudinal cross-section is received by the data analysis device 110. After a preferred position of the cut plane 500 is determined in the longitudinal cross-section, a transversal cross-section of the first blood vessel 210 is displayed, the displayed transversal cross-section being at a location where the hinge point 510 is determined in the longitudinal cross-section.

Alternatively, the location of the cut plane 500 may be determined fully automatically by the microprocessor 112, in which case the microprocessor 112 receives the position data of the cut plane 500 from the microprocessor 112 itself. First, a discontinuity is detected in the vessel wall 212. Such discontinuity may be an abrupt ending in data collected on a vessel wall in a longitudinal cross section or a transversal cross-section. Subsequently, a location of the second blood vessel 220, the side branch, is determined in the vicinity of the discontinuity. Having determined the side branch, a first slope of the second blood vessel 220 is determined using the available OCT probe data. The first slope of the second blood vessel 220 is a basic orientation of the second vessel wall 222 in the view as depicted by FIG. 5, relative to the longitudinal axis 224 of the first blood vessel. Subsequently, the cut plane 500 is determined to be provided perpendicular to the determined slope in the view as depicted by FIG. 5. This determines a longitudinal angle of the cut plane 500 with the longitudinal axis of the first blood vessel 210.

Alternatively, increase of vessel width is determined over a pre-determined trajectory in the first blood vessel 210. If the width of the first blood vessel 210 increases with and/or above a pre-determined width, it is determined that at this location or over this trajectory, the second blood vessel is present as a side branch of the first blood vessel 210. In order to determine at which side of the first blood vessel 210 the second blood vessel 220 starts, increase of distance from a centre line of the first blood vessel 210 and the first vessel wall 212 and/or the second vessel wall 222 is determined. To this end, the radius of the first blood vessel 210 is determined at one and preferably more angles transversal to the axis of the first blood vessel 210. The location of the second blood vessel 220 relative to the first blood vessel 210 is determined as a location where the radius increases most. Alternatively, a slope of a vessel wall is determined as a location and/or angle where a slope increases most.

Having determined the longitudinal angle, a transversal angle may be determined, being the angle of the cut plane with the transversal axis 602 shown by FIG. 6. This may be done by aligning the cut plane 500 with a general orientation of the second vessel wall perpendicular to the view of FIG. 5 and the view of FIG. 6. Subsequently, Cartesian coordinates of a central point or a hinge point of the cut plane 500. are determined such that the cut plane 500 touches the armpit section 480. In this way, the cut plane 500 is positioned perpendicular to the length of the second blood vessel 220.

Figure 7:
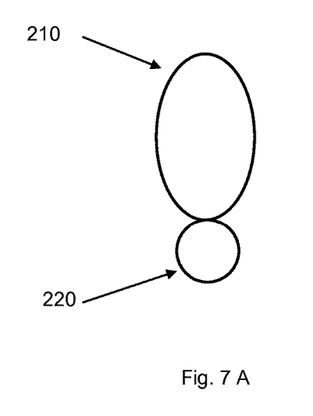

Having received position data of the position of the cut plane 500 in the data set comprising imaging data of the first blood vessel 210 and the second blood vessel 220, cross section image data is determined in step 310. The cross section image data represents a cross section of the first blood vessel 210 and the second blood vessel 220 in the cut plane 500. FIG. 7A shows a cut plane image 700 showing reconstructed image data in the cut plane 500, showing the cross section of the second blood vessel 210 in a substantially circular way. As indicated before, this is an ideal situation not very likely to be found in nature. It is an approximation of a usual situation, though.

FIG. 7B shows the cross section of FIG. 7A in further detail. In the cut plane image 700, a contour 710 is provided in dotted lines, approximating an inner perimeter of the second blood vessel 220. The contour 710 may be generated automatically by determining differences in contrast in data obtained by means of the probe 160. Alternatively, the contour 710 may be drawn by an operator of the data analysis device 110 by means of the keyboard 152, the mouse 154, the touch screen 140, other, or a combination thereof. In another embodiment, the contour 710 is generated automatically and may be adjusted manually. In this way, contour data is obtained in step 312.

Subsequently, using the contour following or at least approximating the inner side of the second vessel wall 222, geometrical parameters of the second blood vessel 220 may be determined. FIG. 7B shows a dashed line 720 through the middle of the contour 710 and crossed by a first marker 722 and a second marker 724. The cross section may be determined as the distance between the first marker 722 and the second marker 724. Also the total area of the lumen of the second blood vessel 220 may be determined using data of the contour 710. This may be done by using data on a determined cross-section and a simple formula. Alternatively, this may be done using numerical calculations. In yet another alternative, two cross-section parameters are determined in directions perpendicular to one another and an area is determined using an elliptical approximation of the shape of the lumen of the second blood vessel. In another embodiment, the curve is a parameterised curve. In this embodiment, parameters determining the curve may be used for determining any geometrical parameter desired to be obtained.

Thus far, various embodiments have been described using data obtained by means of optical coherence tomography. However, the various embodiment may also be used with other techniques suitable for obtaining cross section data sets representing image data of the inside of a blood vessel. This means that the techniques described above may also be used on data obtained by means of intravascular ultrasound or other techniques for obtaining tomographic data within a blood vessel.

The invention claimed is:

1. A method of determining at least one geometrical parameter of a side branch of a main branch of a blood vessel, the method comprising:
   a) receiving a multitude of cross section data sets from within the blood vessel, the data sets representing geometries of cross sections of the main branch over a length of the main branch;
   b) receiving position data of a cut plane of the main branch, the cut plane at least partially intersecting the side branch and the cut plane being non-parallel with the cross sections;
   c) based on data in at least a part of the multitude of cross section data sets, constructing image data of a constructed cross section of the main branch in the cut plane;
   d) receiving contour data defining a contour in the constructed cross section, the contour being provided in the side branch; and
   e) determining the geometrical parameter by determining a geometrical parameter of the contour.

2. The method according to claim 1, wherein the position data comprises angle data indicating an angle between the cut plane and a reference comprised by at least one of the cross section data sets.

3. The method according to claim 1, wherein receiving the definition of the cut plane comprises:
   receiving a longitudinal angle of the cut plane, the longitudinal angle being defined between the cut plane and an axis of the main branch; and
   receiving a transversal angle of the cut plane, the transversal angle being defined between the cut plane and a direction perpendicular to the axis of the main branch.

4. The method according to claim 1, wherein the position data comprises location data indicating a location of the cut plane relative to a reference point comprised by at least one of the cross section data sets.

5. The method according to claim 1, further comprising:
   based on the multitude of cross section data sets, generating first image data for display of a first two-dimensional view of the main branch in a longitudinal direction;
   receiving longitudinal location data of the cut plane indicating a location of the cut plane in the first two-dimensional view;
   based on the multitude of cross section data sets, generating second image data for display of a second two-dimensional view of the main branch in a transversal direction; and
   receiving transversal location data of the cut plane indicating a location of the cut plane in the second two-dimensional view.

6. The method according to claim 5, wherein generating the second image data for display also comprises incorporation of data for displaying a representation of the cut plane in the second two-dimensional view of the main branch based on the longitudinal location data.

7. The method according to claim 5, wherein the generating the first image data for display also comprises incorporation of data for displaying a representation of the cut plane in the first two-dimensional view of the main branch based on the transversal location data.

8. The method according to claim 1, further comprising: determining a discontinuity in a sequential series of the multitude of cross section data sets; and defining the cut plane at the location of the discontinuity as a default location.

9. The method according to claim 8, further comprising:
   determining increase of a cross section geometry parameter being above a pre-determined threshold;
   determining a slope of a side of the main branch relative to a centre line of the main branch;
   determining a first side of the main branch having the largest slope; and defining the cut plane to be positioned substantially perpendicular to the largest slope.

10. The method according to claim 1, wherein the data of the cross section data sets is tomography data.

11. The method according to claim 1, wherein the data of the cross section data sets has been obtained by means of optical coherence tomography.

12. The method according to claim 1, wherein the data of the cross section data sets has been obtained by means of intravascular ultrasound.

13. A computer program product comprising computer executable code that, when loaded in a processing module of a computer, cause the computer to be able to execute the method according to claim 1.

14. A device for determining at least one geometrical parameter of a side branch of a main branch of a blood vessel, the device comprising:
   a data input module arranged to receive a multitude of cross section data sets, the data sets representing geometries of cross sections of the main branch over a length of the main branch;
   a processing unit arranged to:
      receive position data of a cut plane of the main branch, the cut plane at least partially intersecting the side branch and the cut plane being non-parallel with the cross sections;
      based on data in at least a part of the multitude of cross section data sets, construct image data of a constructed cross section of the main branch in the cut plane;
      receive contour data defining a contour in the constructed cross section, the contour being provided in the side branch; and
      determine the geometrical parameter by determining a geometrical parameter of the contour.

* * * * *